US008822382B2

(12) United States Patent
Mir

(10) Patent No.: US 8,822,382 B2
(45) Date of Patent: Sep. 2, 2014

(54) HYDROCOLLOID SYSTEMS FOR REDUCING LOSS OF VOLATILE ACTIVE COMPOUNDS FROM THEIR LIQUID FORMULATIONS FOR PRE- AND POST HARVEST USE ON AGRICULTURAL CROPS

(71) Applicant: Nazir Mir, Somerset, NJ (US)

(72) Inventor: Nazir Mir, Somerset, NJ (US)

( * ) Notice: Subject to any disclaimer, the term of this patent is extended or adjusted under 35 U.S.C. 154(b) by 0 days.

(21) Appl. No.: 13/922,122

(22) Filed: Jun. 19, 2013

(65) Prior Publication Data

US 2014/0011679 A1    Jan. 9, 2014

Related U.S. Application Data

(60) Provisional application No. 61/819,633, filed on May 5, 2013.

(51) Int. Cl.
*A01N 25/00* (2006.01)
*A01N 27/00* (2006.01)
*A01N 25/22* (2006.01)

(52) U.S. Cl.
CPC .............. *A01N 25/22* (2013.01); *A01N 27/00* (2013.01)
USPC ............ 504/140; 504/118; 504/147; 504/357

(58) Field of Classification Search
CPC ....... A01N 25/22; A01N 25/04; A01N 27/00; A01N 25/14; A01N 25/28; A01N 2300/00
USPC .................................. 504/140, 118, 147, 357
See application file for complete search history.

(56) References Cited

U.S. PATENT DOCUMENTS

| | | | |
|---|---|---|---|
| 4,936,901 A * | 6/1990 | Surgant et al. ................. 504/133 |
| 8,377,489 B2 | 2/2013 | Edgington et al. |
| 2007/0207981 A1* | 9/2007 | Almenar et al. ................. 514/58 |
| 2010/0016165 A1* | 1/2010 | Wang et al. ..................... 504/260 |
| 2012/0142534 A1* | 6/2012 | Dahmer et al. ................. 504/357 |
| 2012/0264606 A1 | 10/2012 | Kostansek |
| 2013/0065764 A1 | 3/2013 | Jacobson et al. |

FOREIGN PATENT DOCUMENTS

WO    WO 2006/072180    *  7/2006

* cited by examiner

Primary Examiner — Gina C Justice
Assistant Examiner — Genevieve S Alley
(74) Attorney, Agent, or Firm — Law Office of Stephen P. Krupp, PLLC

(57) ABSTRACT

Ethylene response manipulation formulations are disclosed. The formulations comprise at least one ethylene response manipulation agent which is at least partially encapsulated, a polyol liquid medium, or a hydrogel medium, or a combination of polyol and hydrogel medium. A preferred ethylene response manipulation agent is 1-methylcyclopropene.

7 Claims, 7 Drawing Sheets

HYDROCOLLOID SYSTEMS FOR REDUCING LOSS OF VOLATILE ACTIVE COMPOUNDS FROM THEIR LIQUID FORMULATIONS FOR PRE- AND POST HARVEST USE ON AGRICULTURAL CROPS

RELATED APPLICATIONS

This application is related to and claims priority from U.S. Provisional Patent Application Ser. No. 61/819,633 filed May 5, 2013, the disclosure of which is incorporated herein by reference.

BACKGROUND OF THE INVENTION

Volatile active compounds such as ethylene response manipulation agents or plant disease and insect controlling materials or other plant growth regulating materials are dispersed in water based mediums and sprayed on crops to improve harvest yield, and subsequent storability of harvested plants and plant parts. These compounds are mostly manufactured in concentrated and generally stable forms by either encapsulation process, or forming salts or conjugated complexes for storage and distribution. The concentrated formulations are then dissolved and diluted to desired application concentrations with water or water based mediums immediately prior to their application on agricultural crops. Once the concentrated compounds are dissolved in water or water based mediums, the volatile active compounds on hydration gets released from the liquid formulation, and are lost to the environment or accumulate in the headspace of the formulation or mixing container, as a result the efficacy of the application solution is reduced. Additionally, under most situations, the complete release of the volatile bioactive compound may take less than 1 hour which makes the biological performance of the liquid application almost ineffective under commercially required spray time of at least 3 to 4 hours. Continued volatile loss from liquid solutions containing bioactive volatile compounds can lead to high vapor pressure buildup in the headspace of mixing tank which can cause explosion and risk workers safety.

U.S. Pat. No. 8,377,489 B2 describes the method of contacting bananas with liquid composition comprising a cyclopropene molecular encapsulation agent complex for a period of 1 to 4 minutes. Since the duration of the liquid contact was small, the authors did not investigate the loss of gaseous 1-MCP from the encapsulated matrix in liquid formulation.

US Patent Application Number 2012/0264606 A1 describes an oil medium for suspending encapsulated MCP particles. The authors then process the suspension in the media mill to produce particles of less than 2 micrometers. When the MCP solution was made from these oil based formulations and then passed through the nozzle of a sprayer, the MCP retention in the spray solution was much better. Authors do not report MCP release kinetics from these oil based formulations. As oils are not miscible with water, producing a homogenous solution to cause consistently a desired effect may be a challenge.

US Patent Application Number 2013/0065764 discloses a formulation which comprises suspended MCP encapsulated materials into non-aqueous organic and synthetic fluids and then bringing the formulation into contact with plant and plant parts. The authors' report that the cyclopropene complex in solution remains in the solid form, minimizing the contact between the cyclopropene compound complex and water, leading to the retention of MCP in the solution for a longer time. The authors do not show any MCP release kinetics data. Moreover, the composition of the disclosed formulations may be inapplicable to ripe or near ripe fruit or plant parts due to the potential for undesirably long residual life of some of the synthetic or organic components of the formulation post application.

The disclosed invention comprises of water soluble, environmentally safe and as far as possible, food use approved ingredients that significantly reduce the loss of the volatile active compounds from aqueous solutions leading to sufficient efficacy of liquid formulation or spray solution required to cause a desirable biological effect. The reduction in rapid loss of volatile compounds may help to reduce the volatile accumulation in headspace of mixing tank which can cause potentially explosion hazard in dealing with chemicals of volatile nature. In addition, the invention also improves the half life of spray solution in the mixing tank which makes the spray application more effective, convenient and viable under commercial conditions.

SUMMARY OF THE INVENTION

In one aspect of the invention, a formulation is provided which comprising ethylene response manipulation agents which are substantially non-volatile, with controlled release capability. The formulations comprise: at least one ethylene response manipulation agent which is at least partially encapsulated, a polyol liquid medium, or a hydrogel medium, or a combination of polyol and hydrogel medium, wherein particles are suspended in said medium, wherein said ethylene response manipulation agent comprises cyclopropene, cyclopropene conjugates, cyclopropene salts or cyclopropene encapsulating materials.

The formulation can further comprise at least one plant growth regulator, such as that selected from the group consisting of Gibberellic Acid, Etheral and aminoethoxyvinylglycine. The formulation can further comprise at least one antimicrobial compound, such as that selected from the group consisting of chlorine dioxide, sulphur dioxide, thymol, carvacrol, cinnamaldehyde, allyl isothiocyanate, ethanol, oregano extracts, and other synthetic or natural occurring flavanols, phenolic compounds or organic acids.

In another aspect of the invention, a method of treating the plants or plant parts with the disclosed formulation is provided.

In another aspect of the invention, the droplets formed from the atomizer system and covering the plant canopy hold the encapsulated particles that result into a desired effect.

In another aspect of the invention, a method of controlled release volatiles from the formulation is provided, enabling the liquid formulation to be effective for the desired effect during commercially required time window of longer than one hour. The method comprises at least partially encapsulating at least one ethylene response manipulation agent with at least one encapsulating agent and at least one dispersing or mixing agent selected from the group consisting of a polyol liquid medium, or a hydrogel medium, or a combination of polyol and hydrogel medium, to form an ethylene response manipulation formulation. An added step to the method includes contacting the contacting the ethylene response manipulation formulation with at least one antimicrobial compound, wherein the antimicrobial compound can be selected from the group consisting of chlorine dioxide, sulphur dioxide, thymol, carvacrol, cinnamaldehyde, allyl isothiocyanate, ethanol, oregano extracts, and other synthetic or natural occurring flavanols, phenolic compounds or organic acids In another aspect of the invention, the formulation is dried and converted into granules for direct soil application or in combination with fertilizers for field or fruit crop application.

In another aspect of the invention, a process to make pectin beads or granules comprising of encapsulated 1-MCP particles and/or other components of the formulation are provided for controlling the slow release of 1-MCP from soil application.

In another aspect of the invention, a method is provided for combining the formulation with compostable polymers or flexible films such as polylactic acid (PLA), Polycaprolactone (PCL) and Polyvinyl Alcohol (PVA) or gelatin, converting into granules and then applying the granules direct soil application or in combination with fertilizers for field or fruit crop application.

DETAILED DESCRIPTION OF THE INVENTION

Figure 1:
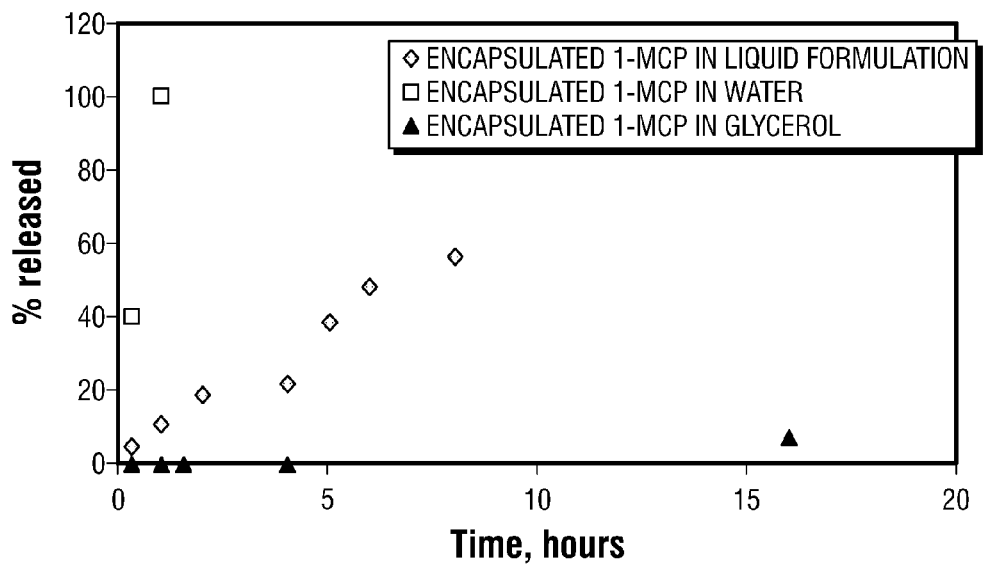
FIG. 1 shows the percentage release of 1-MCP gas from encapsulated 1-MCP dispersed in glycerol, in comparison to water and liquid formulation (Controls). Plotted from Data of Table 1.
Figure 2:
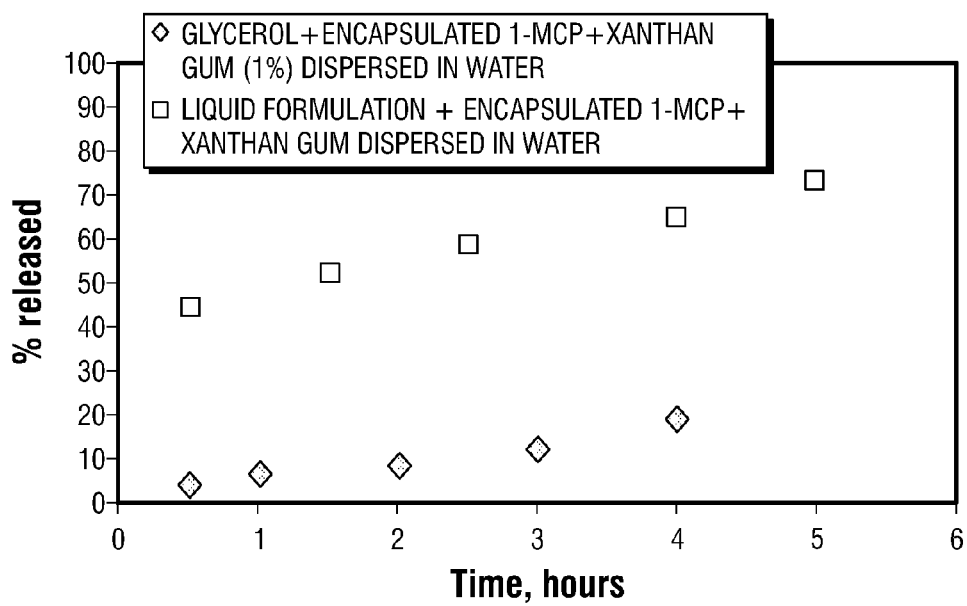
FIG. 2 shows percentage 1-MCP gas released from encapsulated 1-MCP dispersed in glycerol/Xanthan gum system in comparison to liquid formulation/Xanthan gum system (hours). Plotted from Data of Table 2.

Ethylene response manipulation agents include ethylene analogues such as propylene, acetylene, carbon monoxide, 1-butene, etc.; Ethylene releasing compounds such as 2-(chloroethyl) phosphonic acid [commercial name is Etheral], 2-(chloroethylmethyl)bis(phenylmethoxy) silane [commercial name is Silaid], 2-(chloroethyl)tris(2-methoxyethoxy) Silane [commercial name is Alsol]; Ethylene synthesis inhibitors such as aminoethoxyvinylglycine (AVG) [commercial name is RETAIN], aminooxyacetic acid (AOA); and Ethylene action inhibitors such as Silver ions, 2,5-norbornadiene (NBD) and 1-methylcycopropene.

While the invention discloses formulations for encapsulated 1-MCP, a person with ordinary skill and art can use the invention for other control release ethylene manipulation agents as listed above or other chemicals of agricultural importance.

Polyols are used as dispersing agents for cyclodextrin encapsulated 1-methylcyclopropene (1-MCP). Besides cyclodextrin, other encapsulants include those identified in U.S. Patent Application US 2013/0065764 A1, Cucurbit[6] uril by Zhang et. al., (Quan Zhang, Zeng Zhen, Hong Jiang, Xue-Gang Li, and Jun-An Liu. "Encapslation of ethylene inhibitor 1-Methylcyclopropene by Cucurbit[6]uril," Journal of Agricultural and Food Chemistry, 2011, 59: 10539-10545) cyclodextrin nanosponges by Trotta et. al. (Francesco Trotta, Roberta Cavalli, Katia Martina, Miriam Biasizzo, Jenny Vitillo, Silvia Bordiga, Pradeep Vavia and Khalid Ansari. "Cyclodextrin nanosponges as effective gas carriers," Journal of inclusion phenomena and microcyclic chemistry, 2011, 71: 189-194) the disclosures of which are incorporated herein by reference. Cyclodextrin (or some isomerized version of cyclodextrin) is preferred encapsulant. Useful polyols for the invention are glycerol (99.9% pure, Sigma Aldrich Co., St. Louis, Mo.) and D-sorbitol (98% pure, Sigma Chemical Co., St. Louis, Mo.). Other polyols that can be used include di, tri, tetrols and other sugar alcohols, and/or mixtures of these.

One preferred formulation 25 mg of encapsulated 1-MCP are dispersed or mixed in 23 mL of glycerol or D-sorbitol. To make the formulation, the contents are stirred well in a 500 mL mason jar to ensure that 1-MCP particles are uniformly dispersed. Different concentrations of hydrocolloid ranging from 0.005% to 1.0% (w/v) are made by hydrating the hydrocolloid by constantly stirring in water. Hydrocolloids include all hydrophilic polymers dispersed in water Selected examples include hydrocolloids such as Xanthan gum (CP Kelko, Atlanta, Ga.), Carboxy Methyl Cellulose (CMC) (CP Kelko, Atlanta, Ga.), carageenan (CP Kelko), hydroxyl propyl cellulose (Fisher Scientific) and Hydroxyethyl cellulose (Fisher Scientific). Xanthan gum is hydrated by slightly heating the solution, along with stifling it constantly. On completion of hydration, 77 mL of the colloidal solution is stirred and mixed to the polyol/1-MCP dispersion to ensure complete mixing and bring the total volume of the solution to 100 mL. The solution is then placed inside an airtight chamber to quantify the amount of 1-MCP released over time.

Controls (Comparative Examples) used to evaluate the benefit of the invention are (a) 25 mg of encapsulated 1-MCP in water; (b) 25 mg of encapsulated 1-MCP in liquid formulation comprising volatile absorption compounds; (c) 25 mg of encapsulated 1-MCP dispersed or mixed in 2 mL of liquid formulation and the volume made up to 100 mL using 1% hydrated Xanthan gum (comparison is carried out by replacing liquid formulation with glycerol). In all cases, the resultant encapsulated 1-MCP dispersed mixture is placed in an airtight chamber to quantify the amount of 1-MCP released over time.

Quantification of 1-MCP is done using gas chromatography (GC) based on the method described by Mir et al., (Nazir A. Mir, Erin Curell, Najma Khan, Melissa Whitaker, and Randolph M. Beaudry. "Harvest maturity, storage temperature and 1-MCP application frequency alter firmness retention and chlorophyll fluorescence of "Redchief Delicious" apples," Journal of American society of horticultural science, 2001, 126(5): 618-624) 1-MCP gas samples are taken periodically from the chamber and the percentage release is plotted over time to evaluate efficacy of the invention.

The dispersion and release characteristics of encapsulated 1-MCP are done by (a) using polyols alone, (b) combining hydrocolloid with polyol and (c) dispersing compound in colloidal gels.

Dispersion and containment of 1-MCP in polyols is evaluated using 99.9% pure glycerol and 70% solution of D-sorbitol. 25 mg of encapsulated 1-MCP is dispersed in 1 mL of either glycerol or sorbitol. The mixture is then placed in an airtight chamber to quantify the amount of 1-MCP released over time. Quantification of 1-MCP over time is done with GC as described earlier.

Dispersion and containment of 1-MCP in a combination of hydrocolloid and polyol is evaluated by mixing 25 mg of 1-MCP and 25 mg of Xanthan gum. The solid mixture is then dispersed in 23 mL glycerol. The solution is placed in an airtight chamber to quantify the amount of 1-MCP released over time. Quantification of 1-MCP over time is done with GC as described earlier.

Colloidal gels are made by hydrating hydrocolloids with water as a dispersion medium to form a gel or gel like consistency. Xanthan gum and hydroxyl ethyl cellulose are the two hydrocolloids evaluated for the invention. Three concentrations of Xanthan gum are evaluated for the invention. 0.5%, 0.05% and 0.005% xanthan gum is hydrated with water to form colloidal suspensions in low concentrations to weak gels at high concentrations. 25 mg of 1-MCP is dispersed or mixed in 98 mL Xanthan gum solution and stirred well. The mixture is then placed in an airtight chamber to quantify the amount of 1-MCP released over time. Quantification of 1-MCP over time is done with GC as described earlier. Similar invention is done with hydroxy ethyl cellulose (HEC) where 0.05% of colloidal suspension is made with water. 25 mg of 1-MCP is dispersed in 23 mL colloidal solution of HEC and 77 mL of 0.05% solution of Xanthan gum in water is stirred to the mixture. The mixture is then placed in an airtight chamber to quantify the amount of 1-MCP released over time. Quantification of 1-MCP over time is done with GC as described earlier.

The effect of delivering the preferred solution using spraying over a stagnant system is carried out. 25 mg of encapsulated 1-MCP is dispersed in 23 mL glycerol or D-sorbitol. The contents are stirred well in a 500 mL mason jar to ensure that 1-MCP is uniformly dispersed. 0.05% Xanthan gum is hydrated in water and 77 mL of the colloidal solution is mixed with the above 1-MCP/polyol mixture. The percentage 1-MCP released over time is evaluated by (a) placing the mixture in an airtight chamber (stagnant) (b) spraying the mixture in an airtight chamber.

The ability to entrap 1-MCP in a concentrated polyol blend system was evaluated prior to the addition of the water/Xanthan gum system. The effect of 1-MCP release from the concentrated blend of polyol/hydrocolloid/clay without the addition of hydrated colloidal solution was carried out in a 500 mL jar and the amount of 1-MCP released is quantified using GC for 69 hours. The following formulations were evaluated and all contain 25 mg of encapsulated 1-MCP dispersed in the preferred formulation. The formulations evaluated are (1) 0.5 mg of hydroxyl propyl cellulose (HPC) in 10 mL glycerol; (2) 0.25 g of HPC and 0.25 g of laponite in 10 mL of glycerol; (3) 0.5 g of HPC and 0.5 g of laponite in 10 mL glycerol (4) 0.5 g of hydroxyl propyl cellulose (HPC) in 9 mL glycerol and 1 mL of polysorbate (available from Sigma Aldrich); (5) 0.25 g of HPC and 0.25 g of laponite in 9 mL glycerol and 1 mL polysorbate; (6) 0.5 g of HPC and 0.5 g of laponite in 9 mL glycerol and 1 mL polysorbate.

The release rate of 1-MCP on combining the concentrated polyol blend system with water/Xanthan gum mixture was evaluated by dispersing (a) 0.5 g of hydroxyl propyl cellulose (HPC) in 9 mL of glycerol and 1 mL polysorbate or (b) 0.25 g of HPC and 0.25 g of laponite in 9 mL of glycerol and 1 mL polysorbate or (c) 0.5 g of HPC and 0.5 g of laponite in 9 mL glycerol and 1 mL polysorbate (d) 0.5 g of HPC, 0.5 g of laponite and 0.5 g of tetra sodium pyrophosphate in 9 mL glycerol and 1 mL polysorbate. On dispersion, 25 mg of encapsulated 1-MCP is mixed to either solution (a) or (b) or (c) or (d). To make the formulation, the contents are stirred well in a 500 mL mason jar to ensure that 1-MCP is uniformly dispersed. Xanthan gum (0.05% w/v) is hydrated by heating the solution, along with stifling it constantly. On completion of hydration, 90 mL of the colloidal solution is stirred into the encapsulated 1-MCP dispersed formulation (either formulation (a) or (b) or (c) or (d)). The solution is then placed inside an airtight chamber to quantify the amount of 1-MCP released over time.

Addition of maltodextrin to the concentrated polyol blend system was evaluated for its ability to entrap volatile 1-MCP. The formulation is prepared by dispersing (e) 0.5 g of hydroxyl propyl cellulose (HPC) and 0.5 g of maltodextrin in 9 mL glycerol and 1 mL of polysorbate or (f) 0.25 g of HPC, 0.25 g of laponite and 0.5 g maltodextrin in 9 mL glycerol and 1 mL polysorbate. On dispersion, 25 mg of encapsulated 1-MCP is mixed to either solution (e) or (f). To make the formulation, the contents are stirred well in a 500 mL mason jar to ensure that 1-MCP is uniformly dispersed. Xanthan gum (0.05% w/v) is hydrated by heating the solution, along with stirring it constantly. On completion of hydration, 90 mL of the colloidal solution is stirred into the encapsulated 1-MCP dispersed formulation (either formulation (e) or (f). The solution is then placed inside an airtight chamber to quantify the amount of 1-MCP released over time. In order to understand the release profile of 1-MCP and time taken for more than 70% release, 25 mg of encapsulated 1-MCP is dispersed with 0.25 g of HPC and 0.25 g of maltodextrin in 9 mL glycerol and 1 mL of polysorbate. The resultant polyol blend system containing 1-MCP is then mixed with 90 mL of 0.05% (w/v) hydrated Xanthan gum solution. The solution is then placed inside an airtight chamber to quantify the amount of 1-MCP released over time.

The 1-MCP vapor release profile as a function of increase in loading of encapsulated MCP particles to the disclosed formulation of the invention is also shown. Amount of encapsulated 1-MCP in 0.25 g of HPC and 0.25 g of maltodextrin in 9 mL glycerol and 1 mL of polysorbate, was varied from 25 mg to 300 mg and the release is quantified for 3 hours inside an airtight chamber.

Pectin beads containing encapsulated 1-MCP are made first as oil in water emulsion and then gelling with calcium chloride by cross linking. Pectin slurry is made by continuously stirring 5% low methoxy pectin (CP Kelco) in water. Encapsulated 1-MCP emulsion is made by dispersing 25 mg of the encapsulated material in 1 mL of oil and 0.5 mL polysorbate. The oil emulsion is then dispersed in 15 mL of pectin slurry. The resultant oil in water emulsion is then dropped as droplets through a dropper into 1% calcium chloride solution to make the pectin beads. The beads are then filtered and dried. To test the retention of MCP in the beads, 5 grams of pectin beads were added to 95 mL of water and placed for 3 hours in 255 L air tight chamber. The MCP release in the head space of the airtight chamber was measured and it was found that pectin beads retain a significant amount of MCP in the dried form. A person with ordinary skill and art can further improve the method for holding the encapsulated MCP for direct soil application.

In one embodiment, encapsulated bioactive compound, or bioactive compound salts or conjugates such as 1-MCP are dispersed in at least one of the toxicologically acceptable polyols, such as, for example, glycerol, sorbitol, xylitol, manitol, 1,2-propylene glycol or mixtures of these polyols. The polyol or the mixture of polyols is present in the overall composition for dispersion but prior to final dilution for spray application to plant or plant parts is in an amount of 0.1% by weight or more, preferably 1% or more and in particular 5% by weight or more. In some independent embodiments, the polyol or the mixture of polyols is present in the overall composition for dispersion but prior to final dilution for spray application to plant or plant parts is in an amount of 100% by weight or less, preferably 70% by weight or less and in particular 50% by weight or less.

In another embodiment, encapsulated bioactive compound, or bioactive compound salts or conjugates such as 1-MCP are dispersed in at least one of the toxicologically acceptable polyols, such as, for example, glycerol, sorbitol, xylitol, manitol, 1,2-propylene glycol or mixtures of these polyols. The polyol or the mixture of polyols is present in the overall composition in the diluted spray solution for application to plant or plant parts is in an amount of 0.001% by weight or more, preferably 0.01% or more and in particular 0.05% by weight or more. In some independent embodiments, the polyol or the mixture of polyols is present in the overall final composition for plant or plant part application is in an amount of 10% by weight or less, preferably 5% by weight or less and in particular 2% by weight or less.

In another embodiment, the hydrogel agent according to the invention in addition to encapsulated bioactive compound particles, salts or conjugate formulation comprise of at least one binder or thickener, which is present in the compositions according to the invention in a total amount of 0.001% by weight or more, preferably 0.005% or more and in particular 0.05% by weight or more. In some embodiments, in addition to encapsulated bioactive compound particles comprises at least one binder or thickener, which is present in the compositions according to the invention in a total amount of 10% by weight or less, preferably 5% or less and in particular 2% by weight or less. For example, natural and/or synthetic water-soluble polymers, such as xanthan, alginates, carrageens, agar agar, guar gum, gum Arabic, succinoglycan gum, guar flour, carob seed flour, tragacanth, caraya gum, pectins, derivatized celluloses, such as, for example, carboxy-methylcellulose, hydroxyethylcellulose or methyl-hydroxypropylcellulose, hydrophobically modified celluloses, starch and starch ethers are used. Water-soluble carboxyvinyl polymers (e.g. Carbopol grades), polyvinyl alcohol, polyvinylpyrrolidone and higher molecular weight polyethylene glycols (in particular those with molecular weights of 102-106-D) are also suitable for the purpose of the invention. Sheet silicates and finely divided silicas (aerogel silicas and fumed silicas) can likewise be suitable for this application.

Furthermore, gel silcas, xerogel silcas, particulate organic polymers such as polymethacrylate, polyethylene, polypropylene or clay minerals that absorb gasses such as Zeolites or Laponite may be added to the formulation to enhance its efficacy for specific applications. Accordingly, anionic, cationic, nonionic, zwitterionic and ampholytic surfactants with good foam effect may be used to stabilize the formulation and improve application canopy coverage. Oils, fats and wax components can have a complimentary effect on the performance of the application.

In another embodiment, encapsulated bioactive compound, or bioactive compound salts or conjugates such as 1-MCP present in the overall composition of the formulation is in an amount of 0.001% by active ingredient (a.i.) weight or more, preferably 0.005% by a.i. weight or more and in particular 0.05% by a.i. weight or more. In some independent embodiments, encapsulated bioactive compound, or bioactive compound salts or conjugates such as 1-MCP present in the overall composition of the formulation is in an amount of 10% by a.i. weight or less, preferably 5% by a.i. weight or less and in particular 3% by a.i. weight or less.

Bioassay studies are carried out by spraying the preferred solution on tomatoes and the extension in shelf life is recorded. Bioassay of the formulation was performed by spraying the formulation as described above on ripening tomato fruit when they were approximately 50% green, 50% red and held at 22° C. for shelf life evaluation. Compared to the control fruit, where formulation liquid was not sprayed, an extension of 5 days shelf life was observed on fruits sprayed with the formulation. The control fruit had a shelf life of 7 days, while the fruit treated with formulation had a shelf life of 12 days at 22° C.

A related embodiment of the invention is the encapsulation of volatile antimicrobial compounds, where the volatility may vary with temperature, and dispersing the antimicrobial encapsulated material in the polyol or hydrogel or polyol/hydrogel system. The volatile antimicrobials may include chlorine dioxide, sulphur dioxide, thymol, carvacrol, cinnamaldehyde, allyl isothiocyanate, ethanol, oregano extracts and other synthetic or natural occurring flavanols, phenolic compounds or organic acids. The proportion of antimicrobials present in the overall composition of the formulation is in an amount of 0.1 parts per million (ppm, w/v) % or more, preferably 1.0 ppm or more and in particular 10 ppm or more. In some independent embodiments, the amount of antimicrobial compound present in the overall composition of the formulation, is in an amount of 1000 ppm or less, preferably 500 ppm or less and in particular 100 ppm or less.

The encapsulated compounds (or antimicrobial compounds) dispersed in the polyols may be applied alone, in mixtures with each other, or in combination with other ethylene response manipulation agents.

In some embodiments, the proportion of encapsulated 1-MCP to antimicrobial compound present in the formulation is 1:1 or more, preferably 1:100 or more, more preferable 1:1000 or more. In some embodiments, the proportion of encapsulated 1-MCP to antimicrobial compound present in the formulation is 10000:1 or less, preferably 1000:1 or less, more preferable 100:1 or less, either together in the formulation or individually to help maintain quality, prolong shelf life or both. The application of these compounds can be done directly in the field to prevent microbial growth on bruised or cut tissues or post-harvest to prevent spoilage and maintain quality of the food product. The formulation with encapsulated antimicrobial can also be used to help maintain quality and safety of meat, poultry, sea foods, ready to eat meals and other perishable food products, wherein the longevity of the antimicrobials and their activity in the food material would help prevent microbial growth and extend the life of the food product.

In another embodiment, the preferred formulation comprising polyols, or hydrogel, or polyol/hydrogel system, may also contain at least one antioxidant, such as diphenyl amine or ethoxyquin, etc., in addition to encapsulated ethylene response manipulation agents such as 1-MCP for post-harvest application of perishable food products. The antioxidant(s) will help to prevent development of storage disorders of perishable foods such as apple and pear, while as ethylene response manipulation agents will slow ripening and therefore the combined system will deliver an improved quality product at the end of the storage.

In another embodiment, the preferred formulation comprising polyols, or hydrogel, or polyol/hydrogel system, may contain at least one fungicide, insecticide or biopesticide, plant growth regulators such as Gibberellic Acid (GA3), Etheral, aminoethoxyvinylglycine (AVG), etc. or mixtures of these in addition to encapsulated ethylene response manipulation agents such as 1-MCP for pre harvest application of food crops such as fruit, vegetable and field crops. In this latter embodiment, the ethylene response manipulation agent may help scheduling harvests and improving post-harvest life of the crop, while as the fungicides and insecticides will help to control the insects and diseases on the crops. One obvious benefit of this would be to save on cost that is incurred on individual application of these chemicals. In some embodiments, the proportion of encapsulated 1-MCP to pesticide (fungicides, insecticides, bio pesticides, plant growth regulators, etc.) compound present in the formulation is 1:1 or more, preferably 1:100 or more, more preferable 1:1000 or more. In some embodiments, the proportion of encapsulated 1-MCP to pesticide compound present in the formulation is 1000:1 or less, preferably 1000:1 or less, more preferable 100:1 or less.

In another embodiment, the preferred formulation comprising of polyol or hydrogel or polyol/hydrogel system may contain partially encapsulated ethylene response manipulation agents such as 1-MCP for pre or post-harvest application of perishable food crops. The proportion of the partially encapsulated material such as 1-MCP present in the overall composition of the formulation is in an amount of 1% by weight or more, preferably 5% by weight or more and in particular 10% by weight or more, and can be as much as 100%. In some independent embodiments, the partially encapsulated bioactive compound, or bioactive compound salts or conjugates such as 1-MCP present in the overall composition of the formulation, is in an amount of 90% by weight or less, preferably 70% by weight or less and in particular 50% by weight or less.

So, the 1-MCP may be present in an amount of 100 mg/L but only be 30% of that 1-MCP may be encapsulated (30 mg/L); the remaining 70% (70 mg/L) would be "free" 1-MCP (unencapsulated). Some embodiments may have only 10 mg/L 1-MCP of which 90% (9 mg/L) may be completely encapsulated and remaining 10% 1-MCP (1 mg/L) may be in the free form. Likewise some embodiments may have 10,000 mg/L 1-MCP of which 50% (5000 mg/L) is encapsulated and 50% (500 mg/L exists in non-capsulated forms. Depending on the application, the ratio of encapsulated 1-MCP:non-encapsulated 1-MCP can be from about 99:1 to about 50:50, preferably from about 99:1 to about 75:25. Other scenarios of combining encapsulated and non-encapsulated forms of bioactive compounds such as 1-MCP can be formulated by a person with ordinary skills in the art but without deviating from the scope of this invention.

When more than one bioactive compounds such as 1-MCP or other ethylene response manipulation agents and pesticides such as fungicides, insecticides or other plant growth regulators such as Gibberellic Acid (GA3), Etheral, aminoethoxyvinylglycine (AVG), etc. are dispersed in the disclosed formulation to control ripening, modify plant growth and development or to control diseases of plants or plant parts, 1-MCP can be in either encapsulated or non-encapsulated, or combination of both forms, to yield a desired effect of controlling ripening of plant or plant parts. When a mixture of 1-MCP is present in partially encapsulated and partially non-encapsulated form, the proportion of encapsulated to non-encapsulated 1-MCP can be in the ratio of 100:0, or 70:1 or lower or 50:50 or lower. In some embodiments the proportion of encapsulated to non-encapsulated 1-MCP can be in the ratio of 0:100, or 1:70 or higher or 50:50 or higher. So 1-MCP may be present in an amount of 100 mg/L but only 30% of that 1-MCP may be encapsulated (30 mg/L), the remaining 70% (70 mg/L) would be "free" 1-MCP (non-encapsulated). Some embodiments may have only 10 mg/L 1-MCP of which 90% (9 mg/L) may be completely encapsulated and remaining 10% 1-MCP (1 mg/L) may be in the free form. Likewise some embodiments may have 10,000 mg/L 1-MCP of which 50% (5000 mg/L) is encapsulated and 50% (500 mg/L) exists in non-encapsulated forms. Other scenarios of combining encapsulated and non-encapsulated forms of bioactive compounds such as 1-MCP can be formulated by a person with ordinary skills in the art but without deviating from the scope of this invention.

TABLE 1

Percentage release of 1-MCP gas from encapsulated 1-MCP dispersed in glycerol, in comparison to water and liquid formulation (Controls)

| encapsulated 1-MCP in liquid formulation | | encapsulated 1-MCP in water | | encapsulated 1-MCP in Glycerol | |
|---|---|---|---|---|---|
| *100% release of 1-MCP from formulation: 1.45 ppm | | | | | |
| Time (hr) | ppm | % released | Time (hr) | ppm | % released | Time (hr) | ppm | % released |
| 0.25 | 0.074 | 5.13 | 0.25 | 0.586 | 40.42 | 0.25 | 0.000 | 0.00 |
| 1 | 0.157 | 10.92 | 1 | 1.452 | 100.12 | 1 | 0.000 | 0.00 |
| 2 | 0.272 | 18.84 | | | | 1.5 | 0.000 | 0.00 |
| 4 | 0.325 | 22.57 | | | | 4 | 0.000 | 0.00 |
| 5 | 0.569 | 39.45 | | | | 16 | 0.109 | 7.53 |
| 6 | 0.694 | 48.12 | | | | | | |
| 8 | 0.827 | 57.36 | | | | | | |

*Verified by releasing 100% 1-MCP with addition of water in 255.5 L air tight chamber Table 1 demonstrates that 1-MCP gas is released rapidly when encapsulated 1-MCP powder is dissolved in water (reference). The 100% 1-MCP gas release is complete in 1 hour. By comparison, the 1-MCP gas release from liquid formulation of the example is dramatically reduced. It takes approximately 8 hours to release 57.36% of 1-MCP from the liquid formulation, thereby, allowing the liquid formulation to be biologically effective for longer time compared to the reference. When the encapsulated 1-MCP powder was dispersed in glycerol, the release rate of 1-MCP gas from encapsulated powder is drastically reduced, allowing only 7.53% to be released over a 16 hour holding period at Room Temperature of 22° C.

TABLE 2

Percentage 1-MCP gas released from encapsulated 1-MCP dispersed in glycerol/Xanthan gum system in comparison to liquid formulation/Xanthan gum system

| Glycerol + encapsulated 1-MCP + Xanthan gum (1%) dispersed in water | | | liquid formulation + encapsulated 1-MCP + Xanthan gum dispersed in water | | |
|---|---|---|---|---|---|
| *100% release of 1-MCP from formulation: 1.45 ppm | | | | | |
| Time (hours) | ppm | % released | Time (hours) | ppm | % released |
| 0.5 | 0.075 | 5.18 | 0.5 | 0.649 | 44.76 |
| 1 | 0.104 | 7.16 | 1.5 | 0.758 | 52.28 |
| 2 | 0.142 | 9.77 | 2.5 | 0.857 | 59.09 |
| 3 | 0.191 | 13.20 | 4 | 0.944 | 65.09 |
| 4 | 0.295 | 20.37 | 5 | 1.060 | 73.13 |

Table 2 shows that hydrated 1% Xanthan gum in 4 hours releases 20.37% of 1-MCP dispersed in glycerol in comparison to 65.09% released from 1-MCP dispersed in liquid formulation.

TABLE 3

Effect of varying Xanthan gum concentration on the release of 1-MCP gas from encapsulated 1-MCP dispersed in D-sorbitol (70%)
Sorbitol (70%) + encapsulated 1-MCP + Xanthan gum dispersed in water
100% release of 1-MCP from formulation: 1.45 ppm

| Time (min) | 1% XG ppm | 1% XG % released | 0.5% XG ppm | 0.5% XG % released | 0.1% XG ppm | 0.1% XG % released | 0.05% XG ppm | 0.05% XG % released | 0.005% XG ppm | 0.005% XG % released | 0% XG Ppm | 0% XG % released |
|---|---|---|---|---|---|---|---|---|---|---|---|---|
| 0  | 0 | 0.00 | 0 | 0.00 | 0.000 | 0.00 | 0.000 | 0.00 | 0.000 | 0.00  | 0.282 | 19.45  |
| 15 | 0 | 0.00 | 0 | 0.00 | 0.000 | 0.00 | 0.000 | 0.00 | 0.037 | 2.54  | 0.705 | 48.62  |
| 30 | 0 | 0.00 | 0 | 0.00 | 0.021 | 1.46 | 0.014 | 0.95 | 0.123 | 8.51  | 0.974 | 67.17  |
| 45 | 0 | 0.00 | 0 | 0.00 | 0.032 | 2.19 | 0.019 | 1.30 | 0.214 | 14.77 | 1.352 | 93.24  |
| 60 | 0 | 0.00 | 0 | 0.00 | 0.054 | 3.74 | 0.046 | 3.15 | 0.337 | 23.24 | 1.459 | 100.62 |

Different concentrations of Xanthan gum dispersed in water, ranging from 0.005% to 1% is evaluated for their efficacy in controlling release of encapsulated 1-MCP dispersed in D-sorbitol and also compared to the effect of water alone (0% XG in Table 3) in controlling release of encapsulated 1-MCP dispersed in D-sorbitol. The results in Table 3 demonstrate that increasing Xanthan gum concentration in water from 0.005 to 1% slows down the release of encapsulated 1-MCP dispersed in D-sorbitol from 23.24% to 0% in 1 hour. Also replacing Xanthan gum with 100% water (0% XG in Table 3) results in 100% release of encapsulated 1-MCP in 1 hour.

TABLE 4

Effect of varying Xanthan gum concentration on the release of 1-MCP gas from encapsulated 1-MCP dispersed in Glycerol (99.9%)
Glycerol (99.9%) + encapsulated 1-MCP + Xanthan gum dispersed in water
100% release of 1-MCP from formulation: 1.45 ppm

| Time (min) | 1% XG ppm | 1% XG % released | 0.5% XG ppm | 0.5% XG % released | 0.1% XG ppm | 0.1% XG % released | 0.05% XG ppm | 0.05% XG % released | 0.005% XG ppm | 0.005% XG % released | 0% XG ppm | 0% XG % released |
|---|---|---|---|---|---|---|---|---|---|---|---|---|
| 0  | 0 | 0.00 | 0 | 0.00 | 0.000 | 0.00 | 0.000 | 0.00 | 0.000 | 0.00  | 0.356 | 24.55  |
| 15 | 0 | 0.00 | 0 | 0.00 | 0.000 | 0.00 | 0.000 | 0.00 | 0.051 | 3.48  | 0.763 | 52.62  |
| 30 | 0 | 0.00 | 0 | 0.00 | 0.000 | 0.00 | 0.000 | 0.00 | 0.103 | 7.07  | 1.035 | 71.34  |
| 45 | 0 | 0.00 | 0 | 0.00 | 0.047 | 3.21 | 0.006 | 0.41 | 0.108 | 7.48  | 1.455 | 100.34 |
| 60 | 0 | 0.00 | 0 | 0.00 | 0.049 | 3.40 | 0.032 | 2.21 | 0.386 | 26.64 | 1.455 | 100.34 |

Different concentrations of Xanthan gum dispersed in water, ranging from 0.005% to 1% is evaluated for their efficacy in controlling release of encapsulated 1-MCP dispersed in Glycerol and also compared to the effect of water alone (0% XG in Table 4) in controlling release of encapsulated 1-MCP dispersed in Glycerol. The results in Table 4 demonstrate that increasing Xanthan gum concentration in water from 0.005 to 1% slows down the release of encapsulated 1-MCP dispersed in Glycerol from 26.64% to 0% in 1 hour. Also replacing Xanthan gum with 100% water (0% XG in Table 3) results in 100% release of encapsulated 1-MCP in 1 hour.

TABLE 5

Release profile of 1-MCP gas from encapsulated 1-MCP dispersed in sorbitol and in combination with hydrated Xanthan gum
Sorbitol + encapsulated 1-MCP + Xanthan gum (0.025%) dispersed in water
100% release of 1-MCP from formulation: 1.45 ppm

| Time (hr) | ppm | % released |
|---|---|---|
| 0    | 0.000 | 0.00  |
| 0.25 | 0.000 | 0.00  |
| 0.5  | 0.037 | 2.53  |
| 0.75 | 0.078 | 5.40  |
| 1    | 0.130 | 8.94  |
| 1.25 | 0.113 | 7.79  |
| 1.5  | 0.221 | 15.21 |
| 2.25 | 0.357 | 24.61 |
| 3    | 0.465 | 32.05 |
| 19   | 0.973 | 67.14 |

Figure 5:
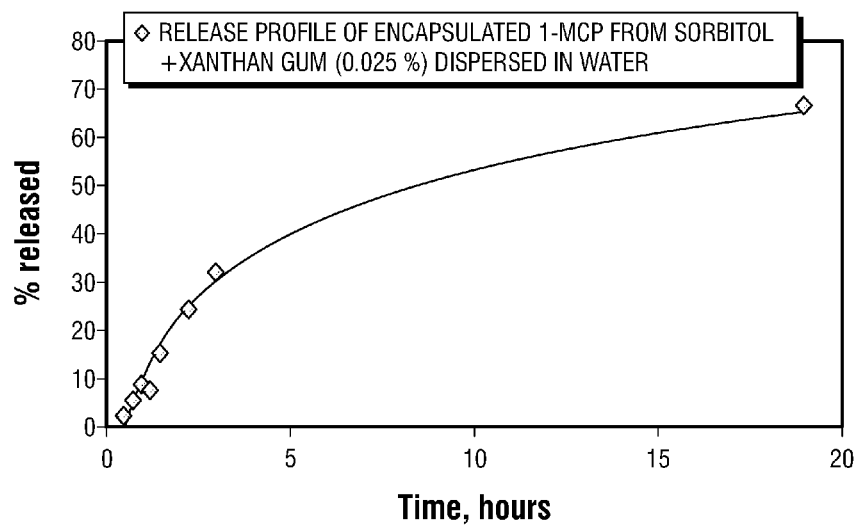
FIG. 5 shows the release profile of 1-MCP gas from encapsulated 1-MCP dispersed in sorbitol and in combination with hydrated Xanthan gum (hours). Plotted from Data of Table 5.

Table 5 and FIG. 5 demonstrate that using hydrated Xanthan gum results in controlled release of encapsulated 1-MCP dispersed in D-sorbitol. About 67% of 1-MCP is released at the end of 19 hours.

TABLE 6

Percentage release of 1-MCP gas when sprayed vs. stagnant from encapsulated 1-MCP dispersed in Glycerol/Xanthan gum/Water or Sorbitol/Xanthan gum/Water system

| Sorbitol + encapsulated 1-MCP + Xanthan gum (0.05%) dispersed in water | | | | | | Glycerol + encapsulated 1-MCP + Xanthan gum (0.05%) dispersed in water | | | | | |
|---|---|---|---|---|---|---|---|---|---|---|---|
| Stagnant | | | Spray | | | Stagnant | | | Spray | | |
| Time (hr) | ppm | % released | Time (hr) | ppm | % released | Time (hr) | ppm | % released | Time (hr) | ppm | % released |
| 0 | 0.000 | 0.00 | 10 | 0.166 | 11.45 | 30 | 0.000 | 0.00 | 0 | 0.000 | 0.00 |
| 15 | 0.000 | 0.00 | 40 | 0.264 | 18.18 | 60 | 0.030 | 2.07 | 15 | 0.044 | 3.02 |
| 30 | 0.028 | 1.91 | 60 | 0.300 | 20.71 | | | | 30 | 0.081 | 5.56 |
| 45 | 0.038 | 2.59 | | | | | | | 45 | 0.126 | 8.66 |
| 60 | 0.091 | 6.29 | | | | | | | 60 | 0.136 | 9.40 |

Figure 6A:
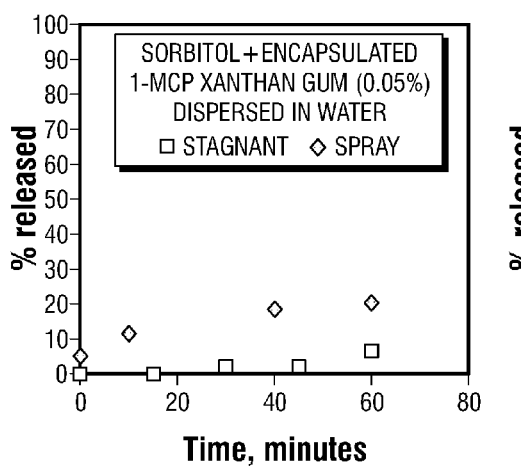
FIG. 6A shows percentage release of 1-MCP gas when sprayed vs. Sorbitol/Xanthan gum/Water system. Plotted from Data of Table 6.
Figure 6B:
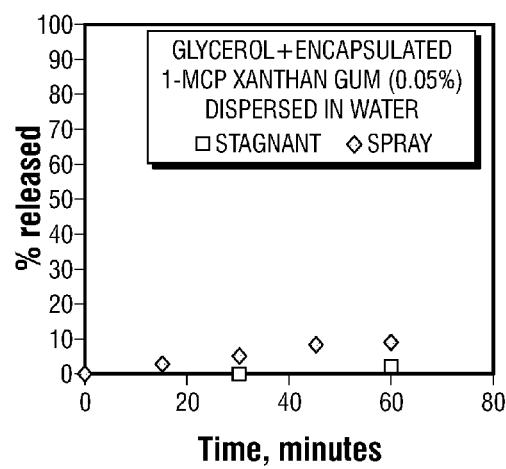
FIG. 6B shows the percentage release of 1-MCP gas when sprayed vs. stagnant from encapsulated 1-MCP dispersed in Glycerol/Xanthan gum/Water.
Figure 7:
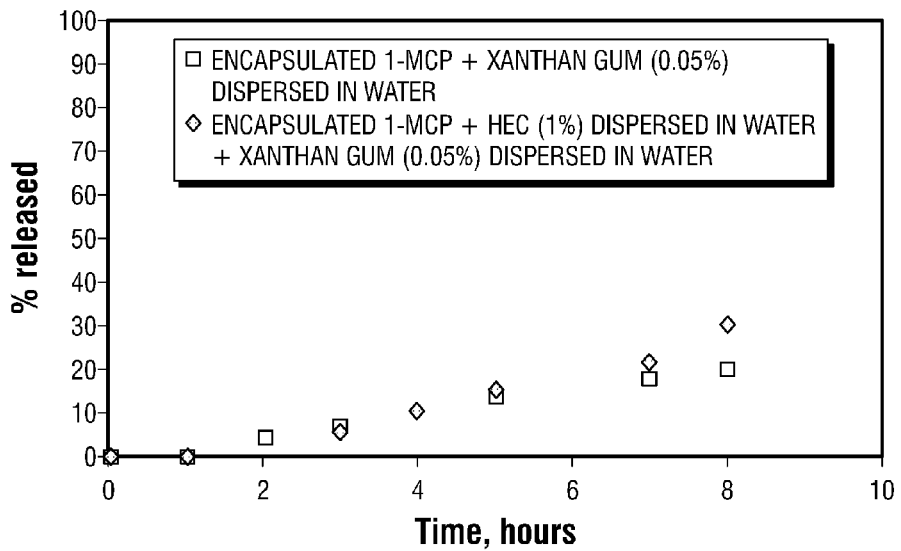
FIG. 7 shows the effect of dispersing encapsulated 1-MCP hydrated Xanthan gum or hydrated Xanthan gum/hydroxyethyl cellulose on its release. Plotted from Data of Table 7.
Figure 8:
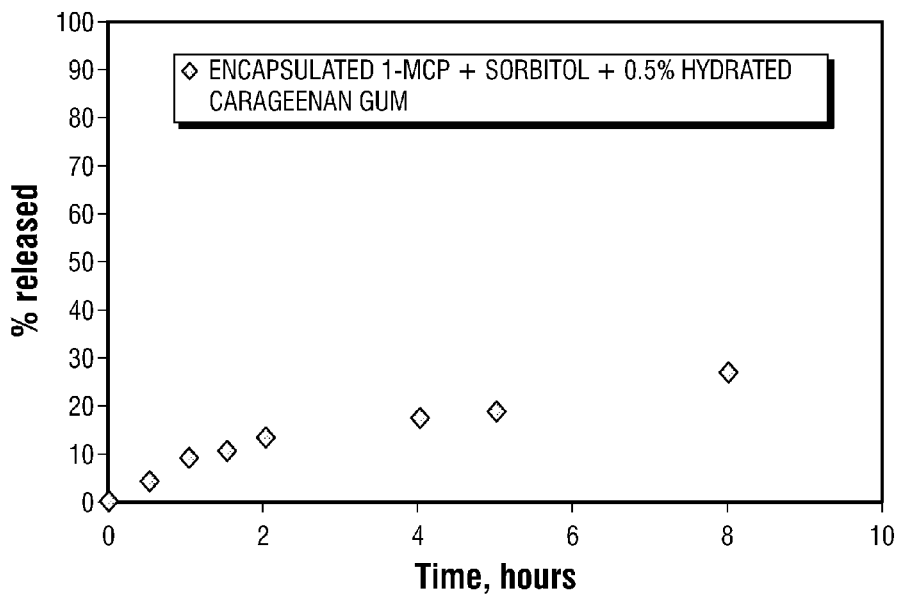
FIG. 8 shows the percentage 1-MCP release from encapsulated 1-MCP dispersed in D-sorbitol mixed with 0.5% hydrated carageenan gum. Plotted from Data of Table 8.
Figure 9:
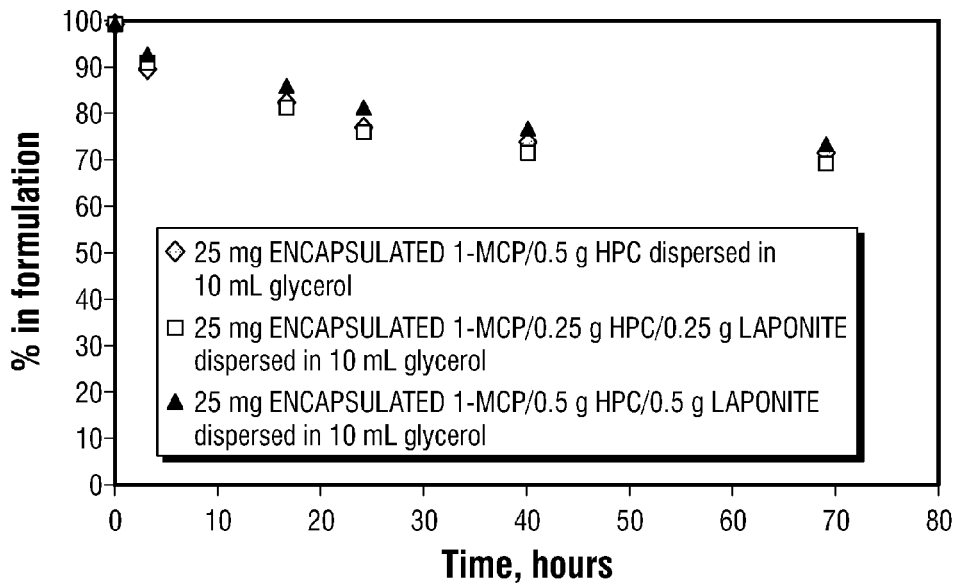
FIG. 9 shows the retention of encapsulated 1-MCP from the glycerol/hydrocolloid or glycerol/hydrocolloid/clay system at room temperature. Plotted from Data of Table 9.
Figure 10:
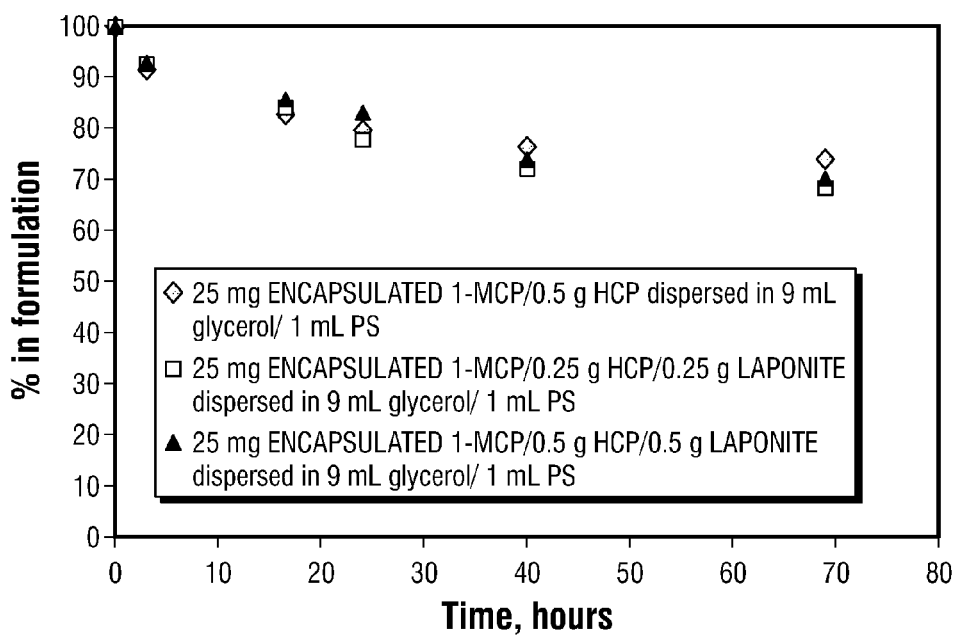
FIG. 10 shows the retention of encapsulated 1-MCP from the glycerol/polysorbate/hydrocolloid or glycerol/polysorbate/hydrocolloid/clay system at room temperature. Plotted from Data of Table 10.
Figure 11:
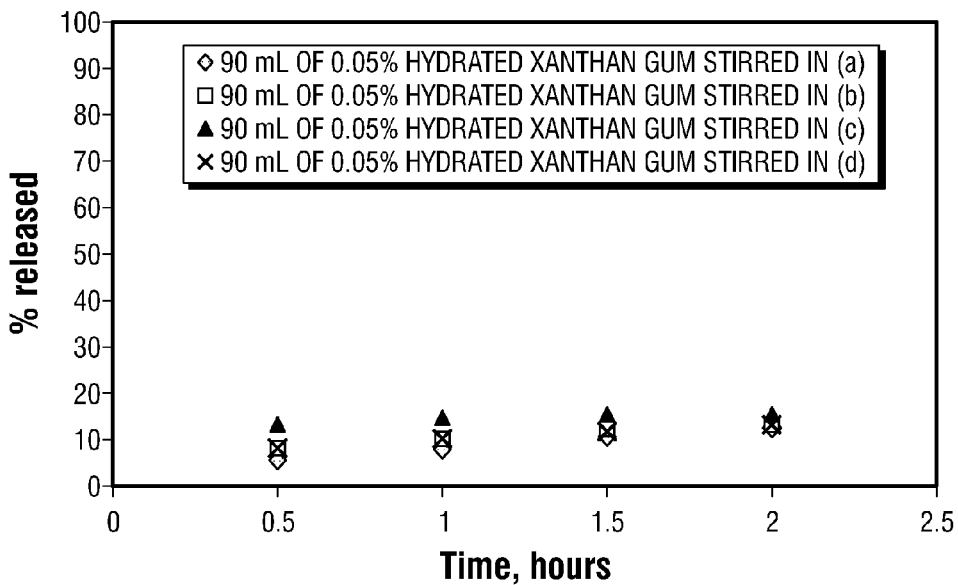
FIG. 11 shows the release of 1-MCP gas from the four formulations (a); (b); (c); (d) when mixed with hydrated 0.05% Xanthan gum. Plotted from Data of Table 11.
Figure 12:
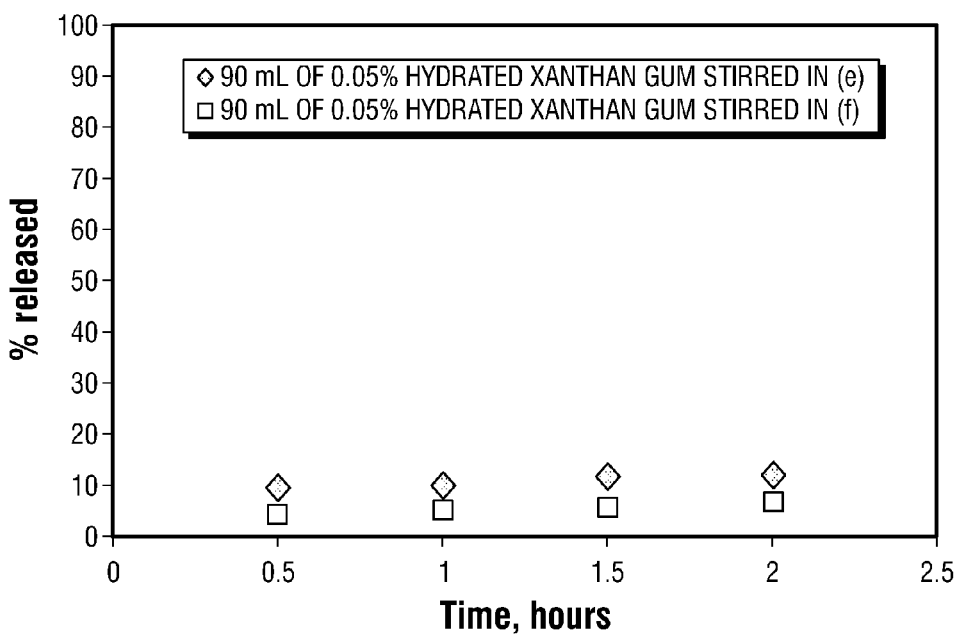
FIG. 12 shows the release of 1-MCP gas from formulations (e); (f) when mixed with hydrated 0.05% Xanthan gum. Plotted from Data of Table 12.
Figure 13:
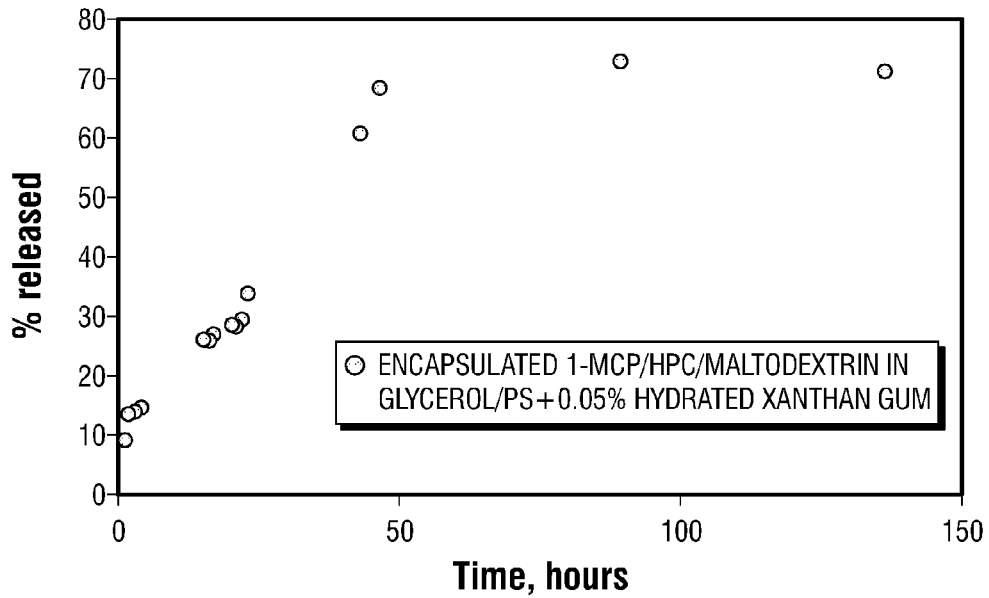
FIG. 13 shows the release profile of 1-MCP gas from polyol blend system when mixed with hydrated 0.05% Xanthan gum. Plotted from Data of Table 13.
Figure 14:
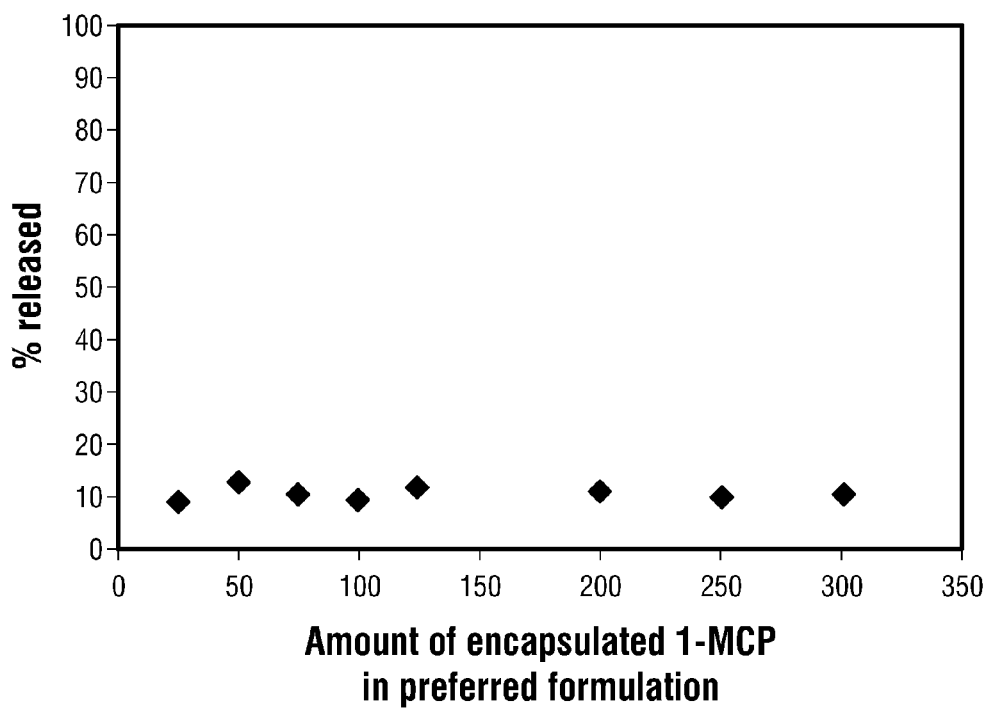
FIG. 14 shows the effect of various encapsulated 1-MCP loading levels on the release profile of 1-MCP gas from the invention. Plotted from Data of Table 14.

Table 6 and FIG. 6 show the effect of decreasing the droplet size of the solution by spraying under pressure vs. not spraying or stagnant on the release of encapsulated 1-MCP from the formulation. In both cases of using glycerol or sorbitol, spraying causes about 3 to 4 times increase in release of encapsulated 1-MCP compared to stagnant in about 60 min, which is still less than 21% compared to 100% release with water (Table 3; table 4; 0% XG).

TABLE 7

Effect of dispersing encapsulated 1-MCP hydrated Xanthan gum or hydrated Xanthan gum/hydroxyethyl cellulose on its release

| encapsulated 1-MCP + Xanthan gum (0.05%) dispersed in water | | | encapsulated 1-MCP + HEC (1%) dispersed in water + Xanthan gum (0.05%) dispersed in water | | |
|---|---|---|---|---|---|
| *100% release of 1-MCP from formulation: 1.45 ppm | | | | | |
| Time (hr) | ppm | % released | Time (hr) | ppm | % released |
| 0 | 0.000 | 0.00 | 0 | 0.000 | 0.00 |
| 1 | 0.000 | 0.00 | 1 | 0.000 | 0.00 |
| 2 | 0.063 | 4.36 | 3 | 0.084 | 5.78 |
| 3 | 0.106 | 7.33 | 4 | 0.153 | 10.56 |
| 5 | 0.206 | 14.19 | 5 | 0.216 | 14.87 |
| 7 | 0.257 | 17.74 | 7 | 0.311 | 21.47 |
| 8 | 0.294 | 20.30 | 8 | 0.444 | 30.62 |

Table 7 demonstrates the effect of hydrated xanthan gum or hydrated xanthan gum in combination with hydrated hydroxyethyl cellulose in controlling the release of encapsulated 1-MCP. In both cases the data shows 20-30% release of 1-MCP in 8 hours. Hydrated xanthan gum, by itself, seems more effective in slowing the release of encapsulated 1-MCP to about 20% in 8 hours compared to its combination with hydroxyethyl cellulose, where the release is around 30% in 8 hours.

TABLE 8

Percentage 1-MCP release from encapsulated 1-MCP dispersed in D-sorbitol mixed with 0.5% hydrated carageenan gum Sorbitol + encapsulated 1-MCP + carageenan gum (0.5%) dispersed in water

*100% release of 1-MCP from formulation: 1.45 ppm

| Time (hr) | ppm | % released |
|---|---|---|
| 0 | 0.000 | 0.00 |
| 0.5 | 0.058 | 3.98 |
| 1 | 0.129 | 8.87 |
| 1.5 | 0.153 | 10.55 |
| 2 | 0.191 | 13.20 |
| 4 | 0.246 | 16.97 |
| 5 | 0.267 | 18.41 |
| 8 | 0.388 | 26.77 |

Table 8 shows that encapsulated 1-MCP dispersed in sorbitol when mixed with other hydrocolloid such as carageenan gum (0.5%) dispersed in water also helps in controlling the release of 1-MCP. The table shows about 26.77% of 1-MCP released in 8 hours, compared to 100% release with water in 1 hour (Table 3; table 4; 0% XG).

TABLE 9

Retention of encapsulated 1-MCP from the glycerol/hydrocolloid or glycerol/hydrocolloid/clay system at room temperature

| | encapsulated 1-MCP/HPC dispersed in glycerol | | encapsulated 1-MCP/HPC/Laponite dispersed in glycerol | | encapsulated 1-MCP/HPC/Laponite dispersed in glycerol | |
|---|---|---|---|---|---|---|
| Time hr | ppm | % in the formulation | ppm | % in the formulation | ppm | % in the formulation |
| 0 | 3.33 | 99.61 | 0.84 | 99.90 | 2.74 | 99.68 |
| 3 | 78.86 | 90.73 | 68.15 | 91.99 | 55.62 | 93.46 |
| 16.5 | 145.84 | 82.86 | 153.77 | 81.92 | 116.27 | 86.33 |
| 24 | 191.90 | 77.44 | 197.28 | 76.81 | 154.10 | 81.89 |
| 40 | 220.06 | 74.13 | 236.73 | 72.17 | 192.46 | 77.38 |
| 69 | 237.44 | 72.09 | 259.76 | 69.46 | 222.91 | 73.80 |

Table 9 shows that 1-MCP gas released at room temperature, is only ≤31% (69% of 1-MCP left in the formulation) in a period of 69 hours, when a concentrated blend of glycerol/HPC (hydrocolloid) or glycerol/HPC/Laponite (clay) system containing encapsulated 1-MCP is left as such without the addition of water or a hydrated hydrocolloid.

TABLE 10

Retention of encapsulated 1-MCP from the glycerol/polysorbate/hydrocolloid or glycerol/polysorbate/hydrocolloid/clay system at room temperature

| Time hr | encapsulated 1-MCP/HPC dispersed in glycerol/PS | | encapsulated 1-MCP/HPC/0.25 g Laponite dispersed in glycerol/PS | | encapsulated 1-MCP/HPC/Laponite dispersed in glycerol/PS | |
|---|---|---|---|---|---|---|
| | ppm | % in the formulation | ppm | % in the formulation | ppm | % in the formulation |
| 0 | 2.59 | 99.70 | 0.76 | 99.91 | 0.90 | 99.89 |
| 3 | 60.84 | 92.85 | 56.78 | 93.33 | 55.05 | 93.53 |
| 16.5 | 143.02 | 83.19 | 130.25 | 84.69 | 117.99 | 86.13 |
| 24 | 165.29 | 80.57 | 184.56 | 78.30 | 134.81 | 84.15 |
| 40 | 195.80 | 76.98 | 230.19 | 72.94 | 213.17 | 74.94 |
| 69 | 216.63 | 74.54 | 263.22 | 69.06 | 252.62 | 70.30 |

Figure 3:
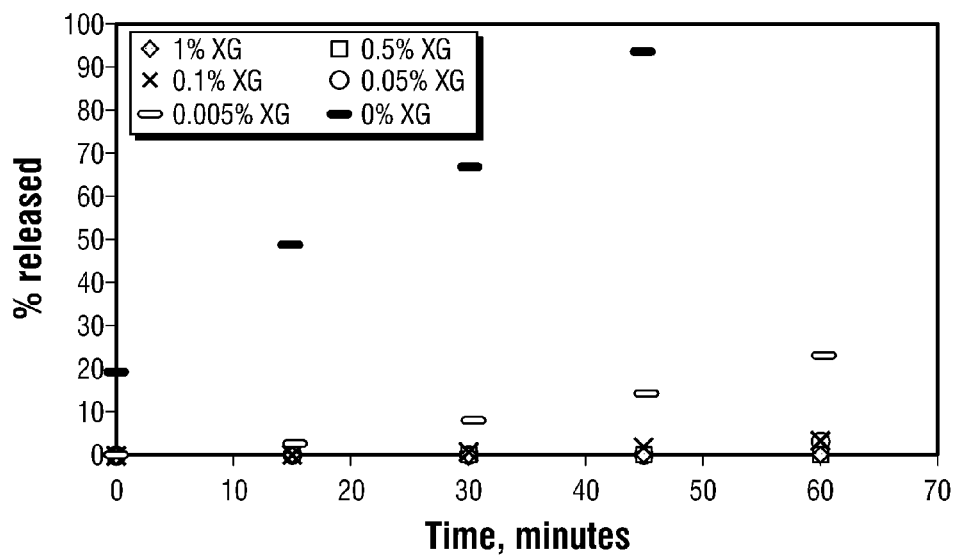
FIG. 3 shows the effect of varying Xanthan gum concentration on the release of 1-MCP gas from encapsulated 1-MCP dispersed in D-sorbitol (70%). Plotted from Data of Table 3.
Figure 4:
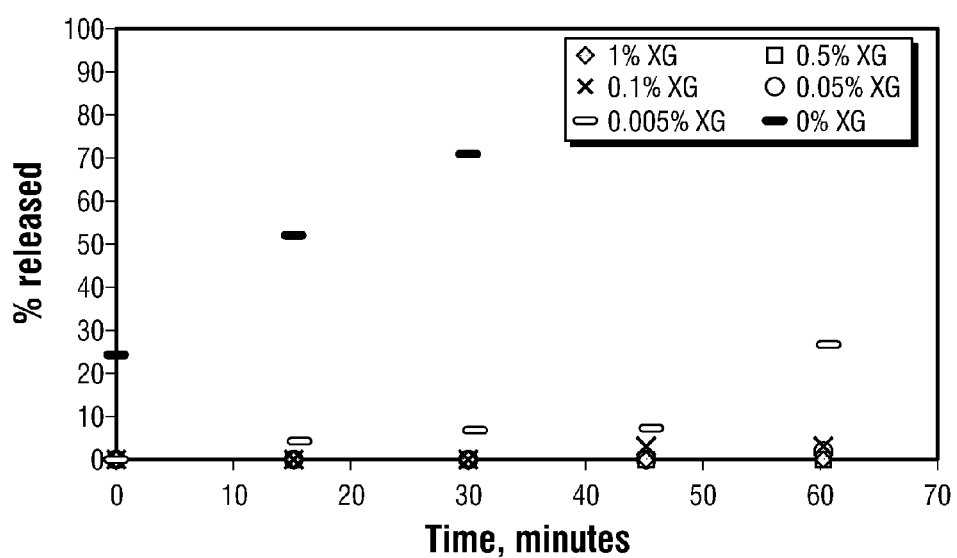
FIG. 4 shows the effect of varying Xanthan gum concentration on the release of 1-MCP gas from encapsulated 1-MCP dispersed in Glycerol (99.9%). Plotted from Data of Table 4.

Table 10 shows the effect of adding an emulsifier such as polysorbate to the concentrated blend of glycerol/HPC (hydrocolloid) or glycerol/HPC/Laponite (clay) system containing encapsulated 1-MCP and left as such without the addition of water or a hydrated hydrocolloid. The resultant system shows that 1-MCP gas released at room temperature is only ≤31% (69% of 1-MCP left in the formulation) in a period of 69 hours. By comparison, comparative formulation comprising of water plus encapsulated 1-MCP does not retain 1-MCP beyond 1 hour of holding (see table 3 and FIG. 3).

TABLE 11

Release of 1-MCP gas from the four formulations (a); (b); (c); (d) when mixed with hydrated 0.05% Xanthan gum 0.05% hydrated Xanthan gum stirred in (a); (b); (c) and (d)

| Time | (a) encapsulated 1-MCP/HPC dispersed in glycerol/PS | | (b) encapsulated 1-MCP/HPC/Laponite dispersed in glycerol/1 mL PS | | (c) encapsulated 1-MCP/HPC/Laponite dispersed in glycerol/PS | | (d) encapsulated 1-MCP/HPC/Laponite/TSPP dispersed in glycerol/PS | |
|---|---|---|---|---|---|---|---|---|
| hr | ppm | *% released | ppm | *% released | ppm | *% released | ppm | *% released |
| 0.5 | 0.09 | 6.31 | 0.12 | 8.09 | 0.19 | 13.28 | 0.13 | 9.17 |
| 1 | 0.12 | 8.25 | 0.15 | 10.61 | 0.21 | 14.71 | 0.15 | 10.57 |
| 1.5 | 0.16 | 10.97 | 0.19 | 12.89 | 0.23 | 15.85 | 0.17 | 11.80 |
| 2 | 0.19 | 13.19 | 0.20 | 13.91 | 0.23 | 15.68 | 0.19 | 12.91 |

Table 11 demonstrates that 1-MCP release is controlled to about 13-16% in 2 hours when the encapsulated 1-MCP is blended to formulations (a); (b); (c) and (d) and hydrated Xanthan gum solution is added to the blend.

TABLE 12

Release of 1-MCP gas from formulations (e); (f) when mixed with hydrated 0.05% Xanthan gum 0.05% hydrated Xanthan gum stirred in (e) and (f)

| Time | (e) encapsulated 1-MCP/HPC/Maltodextrin dispersed in glycerol/PS | | (f) encapsulated 1-MCP/HPC/Laponite/Maltodextrin dispersed in glycerol/PS | |
|---|---|---|---|---|
| hr | ppm | % released | ppm | % released |
| 0.5 | 0.13 | 9.09 | 0.06 | 4.47 |
| 1 | 0.14 | 9.74 | 0.08 | 5.25 |
| 1.5 | 0.16 | 11.20 | 0.09 | 6.05 |
| 2 | 0.17 | 12.00 | 0.10 | 6.70 |

Table 12 shows that the addition of maltodextrin to formulations (e) and (f) regulates the release of 1-MCP to about 12% in formulation (e) and to about 6.7% in formulation (f), when stirred with hydrated Xanthan gum solution.

TABLE 13

Release profile of 1-MCP gas from polyol blend system when mixed with hydrated 0.05% Xanthan gum encapsulated 1-MCP/HPC/Maltodextrin in glycerol/PS mixed with 0.05% hydrated Xanthan gum

| time, hr | ppm | *% released |
|---|---|---|
| 1 | 0.118886 | 9.700 |
| 2 | 0.168817 | 13.775 |
| 3 | 0.172454 | 14.071 |
| 4 | 0.181956 | 14.847 |
| 15 | 0.323141 | 26.366 |
| 16 | 0.319817 | 26.095 |
| 17 | 0.334142 | 27.264 |
| 20 | 0.351606 | 28.689 |
| 21 | 0.349041 | 28.480 |
| 22 | 0.366497 | 29.904 |
| 23 | 0.418878 | 34.178 |
| 43 | 0.745569 | 60.834 |
| 46.5 | 0.840453 | 68.576 |
| 89 | 0.894203 | 71.344 |
| 136 | 0.874369 | 72.962 |

Table 13 demonstrates that about 73% 1-MCP is released in 5.6 days, when encapsulated 1-MCP is dispersed in polyol blend system (glycerol/polysorbate/HPC/maltodextrin) and mixed with hydrated Xanthan gum solution.

TABLE 14

Effect of various encapsulated 1-MCP loading levels on the release profile of 1-MCP gas from the invention encapsulated 1-MCP/HPC/Maltodextrin dispesed in glycerol/PS

| Amount of encapsulated 1-MCP (mg) | % released in 3 hours |
|---|---|
| 25 | 9.01 |
| 50 | 12.56 |
| 75 | 10.47 |
| 100 | 9.04 |
| 125 | 11.75 |
| 200 | 10.65 |
| 250 | 9.57 |
| 300 | 10.20 |

Table 14 shows that varying amounts of 1-MCP from 25 mg to 300 mg in polyol blend system (glycerol/polysorbate/HPC/maltodextrin), does not dramatically change the percentage of 1-MCP lost from the formulation. In all cases, the release seems to vary between 9 to 13% in 3 hours. This clearly demonstrates the suitability of the invention for a wide range of active compound holding and subsequent controlled or slow release for application.

The invention claimed is:

1. An ethylene response manipulation formulation for contacting a plant or a plant part consisting essentially of at least one ethylene response manipulation agent which is at least partially encapsulated to form particles, from 0.001 weight percent to 10 weight percent of a polyol liquid medium, wherein the particles are dispersed or mixed in said medium, wherein said ethylene response manipulation agent comprises cyclopropene, cyclopropene conjugates, cyclopropene salts or cyclopropene encapsulating materials.

2. The formulation of claim 1 wherein the ethylene response manipulation agent is 1-methylcyclopropene (1-MCP).

3. The formulation of claim 1 in the form of granules, for direct soil application or in combination with fertilizers for field or fruit crop application.

4. The formulation of claim 2 wherein a ratio of encapsulated to non-encapsulated 1-methylcyclopropene (1-MCP) is about 99:1 to about 50:50.

5. An ethylene response manipulation formulation for contacting a plant or a plant part consisting essentially of at least one ethylene response manipulation agent which is at least partially encapsulated to form particles, from 0.001 weight percent to 10 weight percent of a hydrogel medium, wherein the particles are dispersed or mixed in said medium, wherein said ethylene response manipulation agent comprises cyclopropene, cyclopropene conjugates, cyclopropene salts or cyclopropene encapsulating materials.

6. An ethylene response manipulation formulation for contacting a plant or a plant part consisting essentially of at least one ethylene response manipulation agent which is at least partially encapsulated to form particles, from 0.001 weight percent to 10 weight percent of a combination of polyol and hydrogel medium, wherein the particles are dispersed or mixed in said medium, wherein said ethylene response manipulation agent comprises cyclopropene, cyclopropene conjugates, cyclopropene salts or cyclopropene encapsulating materials.

7. The formulation of claim 6 wherein the polyol is glycerol, the hydrogel is selected from the group consisting of hydroxypropyl cellulose, maltodextrin, hydrated xanthan gum, and mixtures thereof, the particles are encapsulated with cyclodextrin or isomerized cyclodextrin, the ethylene response manipulation agent is 1-MCP, and wherein not more than 73% of the 1-MCP is released in 5.6 days.

* * * * *